(12) United States Patent
Nakanishi

(10) Patent No.: US 8,031,830 B2
(45) Date of Patent: Oct. 4, 2011

(54) X-RAY CT APPARATUS AND METHOD OF CONTROLLING A COLLIMATOR AND AN ANGLE TO ACQUIRE X-RAY DATA

(75) Inventor: Satoru Nakanishi, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 121 days.

(21) Appl. No.: 12/126,617

(22) Filed: May 23, 2008

(65) Prior Publication Data
US 2008/0298539 A1 Dec. 4, 2008

(30) Foreign Application Priority Data

May 31, 2007 (JP) ................................. 2007-146084
May 31, 2007 (JP) ................................. 2007-146085

(51) Int. Cl.
*A61B 6/00* (2006.01)
(52) U.S. Cl. .......................................... 378/15; 378/19
(58) Field of Classification Search ................ 378/4, 15, 378/19
See application file for complete search history.

(56) References Cited

U.S. PATENT DOCUMENTS

| | | | | |
|---|---|---|---|---|
| 5,170,439 A | * | 12/1992 | Zeng et al. | 382/131 |
| 5,706,325 A | * | 1/1998 | Hu | 378/4 |
| 6,014,419 A | * | 1/2000 | Hu | 378/4 |
| 6,445,761 B1 | * | 9/2002 | Miyazaki et al. | 378/8 |
| 6,546,067 B2 | | 4/2003 | Aradate et al. | |
| 6,650,308 B2 | * | 11/2003 | Kawashima | 345/76 |
| 2003/0068005 A1 | * | 4/2003 | Yamazaki | 378/4 |
| 2004/0141581 A1 | * | 7/2004 | Bruder et al. | 378/4 |
| 2004/0174960 A1 | * | 9/2004 | Hsieh et al. | 378/210 |
| 2005/0053188 A1 | * | 3/2005 | Gohno | 378/15 |
| 2006/0034417 A1 | * | 2/2006 | Katsevich | 378/4 |
| 2007/0053478 A1 | * | 3/2007 | Tsuyuki et al. | 378/4 |

FOREIGN PATENT DOCUMENTS

JP 2002-360562 12/2002

OTHER PUBLICATIONS

U.S. Appl. No. 12/169,963, filed Jul. 9, 2008, Nakanishi, et al.

* cited by examiner

*Primary Examiner* — Edward Glick
*Assistant Examiner* — Alexander H Taningco
(74) *Attorney, Agent, or Firm* — Oblon, Spivak, McClelland, Maier & Neustadt, L.L.P.

(57) ABSTRACT

In an X-ray CT apparatus, the X-ray tube generates an X-ray beam during a line-orbit scan, and the collimator plate shields a part of the X-ray beam other than the part that contributes to image reconstruction. The part of the X-ray beam which contributes to the image reconstruction is applied to a subject along the body axis of the subject. The two-dimensional detector system detects the X rays in the same conditions during a circular-orbit scan, while the X-ray tube and the subject are rotating relative to each other. The reconstruction device performs back projection, thereby reconstructing an image.

8 Claims, 10 Drawing Sheets

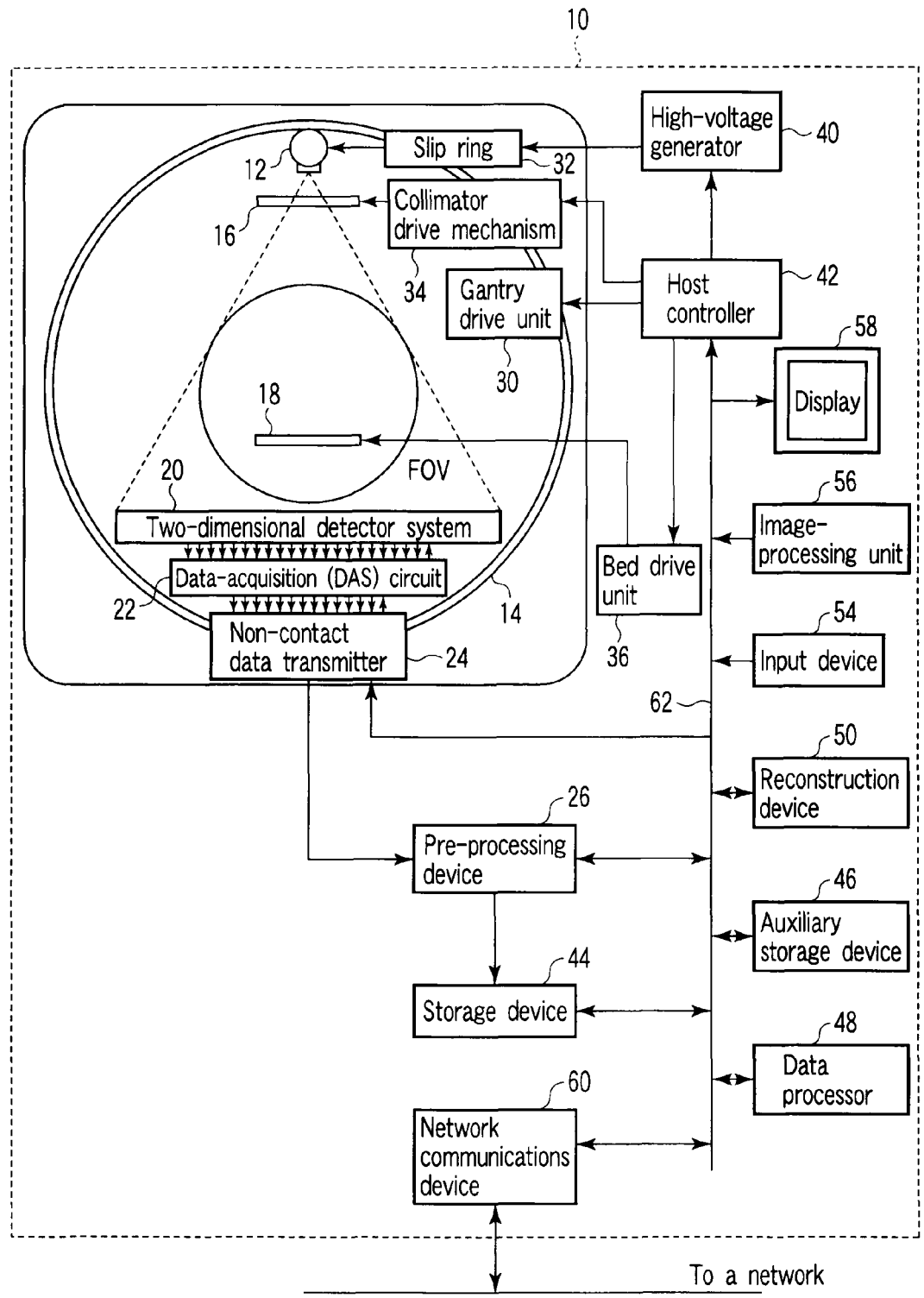
F I G. 1

1 mm × 2 rows 0.5mm × 256 rows

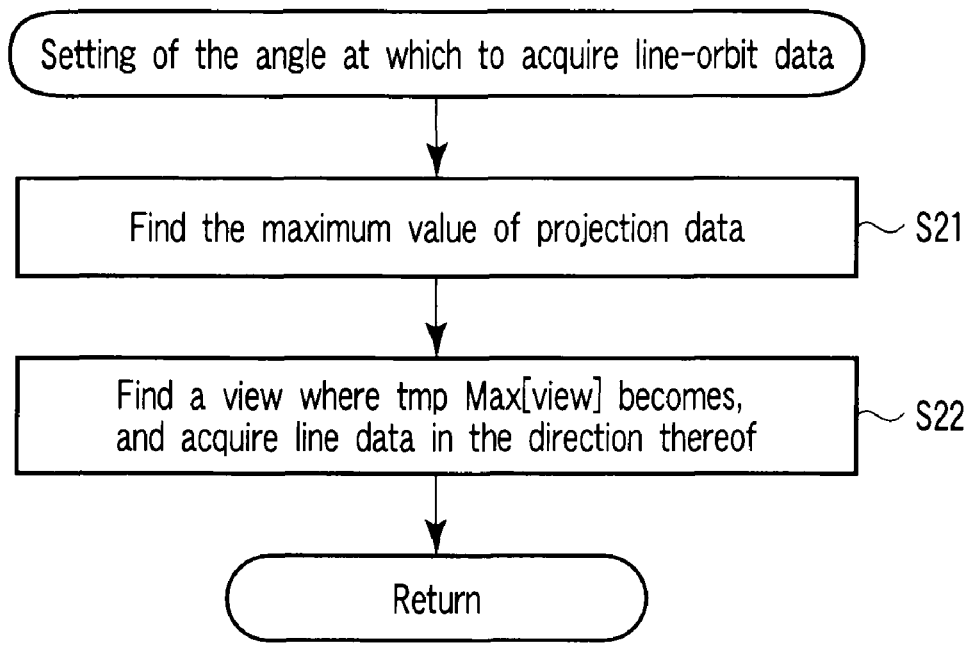
F I G. 15
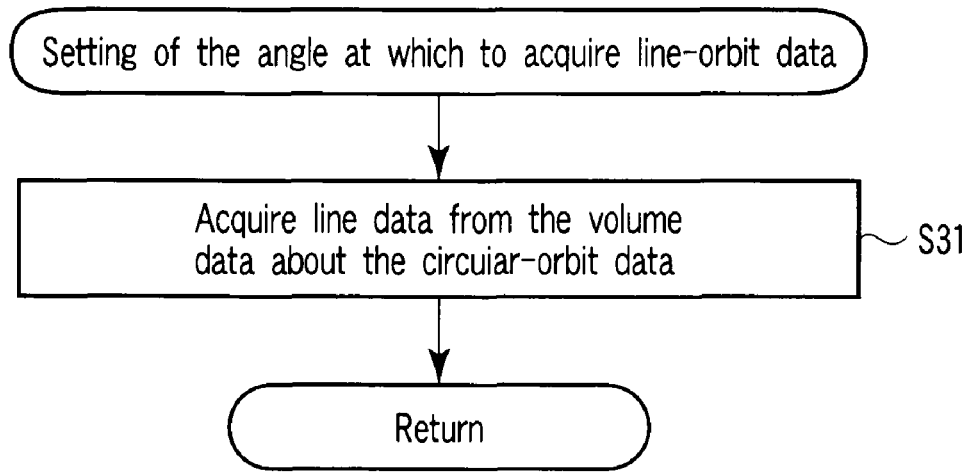
F I G. 16

X-RAY CT APPARATUS AND METHOD OF CONTROLLING A COLLIMATOR AND AN ANGLE TO ACQUIRE X-RAY DATA

CROSS-REFERENCE TO RELATED APPLICATIONS

This application is based upon and claims the benefit of priority from prior Japanese Patent Applications No. 2007-146084, filed May 31, 2007; and No. 2007-146085, filed May 31, 2007, the entire contents of both of which are incorporated herein by reference.

BACKGROUND OF THE INVENTION

1. Field of the Invention

The present invention relates to an X-ray CT apparatus that performs cone-beam reconstruction and a method of controlling the X-ray CT apparatus. More particularly, the invention relates to an X-ray CT apparatus that applies X rays to a living subject, providing information about the interior of the subject in the form of an image.

2. Description of the Related Art

In recent years, a system has been defined as a third-generation CT apparatus. This system comprises an X-ray tube and an X-ray detector. The X-ray tube generates an X-ray beam. The X-ray detector is located, opposing the X-ray tube, with the subject lying in between. As the X-ray tube and X-ray detector rotate around the subject, projection data items are acquired from various angles. Hitherto, the X-ray beam is a fan-shaped beam and the detector is a one-dimensional array detector.

Scanning systems are available in two types, i.e., conventional scan system and helical scan system. The conventional scan system is defined as a circular-orbit scan system in which the X-ray tube moves in one circular orbit. The helical scan system is defined as scan system in which the X-ray source and the X-ray detector keeps rotating around the subject and the bed supporting the subject moves along the body axis of the subject. The helical scan system is so named, because the X-ray tube is considered to move in a helical orbit in view of the coordinates system that moves as the subject is moved. Note that the distance the subject is moved along the body axis, i.e., Z axis, every time the X-ray tube rotates around the subject is defined as helical pitch.

Among the third- and fourth-generation CT apparatuses recently developed are a CT apparatus having a new-type X-ray tube and a two-dimensional array detector. The new-type X-ray tube generates not a fan-shaped X-ray beam, but a cone-shaped X-ray beam that diverges, like a cone, in the body axis of the subject. This CT apparatus is called a cone-beam CT apparatus. The two-dimensional array detector has a plurality of one-dimensional array detectors, each consisting of detector elements. These detectors, for example, N detectors, are laid one on another in the Z-axis direction. Thus, the detector elements are arranged in rows and columns, forming a matrix.

Known as a method of providing tomograms, using the conventional scan system, is the circular-orbit, cone-beam reconstruction method proposed by Feldkamp et al. (See, for example, Jon. Pat. Apply. KOKAI Publication No. 2002-360562.) However, cone-beam artifacts develop in the circular-orbit, cone-beam reconstruction method. Consequently, this method cannot provide perfect data. The method has been proved to degrade the image in quality.

In order to solve this problem, a new cone-beam reconstruction method has been proposed. This new method is known as a line+cicle reconstruction method (hereinafter called line-circle reconstruction method). In recent years, Katsevich et al. have proposed a line-circle reconstruction method, which is known as the "filter+back projection" system.

To implement the line-circle reconstruction method successfully, the following requirements should be satisfied.

Since line data is regarded as an additional scan, or an excessive exposure, an additional exposure, if any, must be reduced as much as possible. Further, only a part of line data contributes to the reconstruction and the remaining part is, therefore, a wasteful exposure, though the line data should be large cone-angle data.

BRIEF SUMMARY OF THE INVENTION

Accordingly, an object of the present invention is to provide an X-ray CT apparatus in which the collimator is operated during a line-orbit scan, changing the X-ray applying width as measured in the slice direction and reducing the X-ray application to a part that does not contribute to image reconstruction, and also to provide a method of controlling the X-ray CT apparatus.

More precisely, an object of the invention is to provide an X-ray CT apparatus that has an X-ray source which generates an X-ray beam diverging along a body axis of a subject, and X-ray detecting unit including detecting elements arranged in rows, along the body axis of the subject and configured to detect X rays that have passed through the subject. The X-ray apparatus comprises: scan control unit for performing control, thereby acquiring first projection data while moving the X-ray source, relative to the subject, along the body axis of the subject, and acquiring second projection data while rotating the X-ray source around the subject; X-ray shielding unit for changing, while the first projection data is being acquired, an amount by which the X-ray beam generated by the X-ray source is shielded in accordance with a position where the first projection data is acquired; and reconstruction mans for synthesizing the first projection data partly shielded by the X-ray shielding unit, with the second projection data, thereby performing a reconstruction process.

Another object of the invention is to provide an X-ray CT apparatus having an X-ray source which generates an X-ray beam diverging along a body axis of a subject, and X-ray detecting unit including detecting elements arranged in rows, along the body axis of the subject and configured to detect X rays that have passed through the subject. This X-ray CT apparatus comprises: first scan control unit for performing a control, thereby acquiring first projection data while moving the X-ray source, relative to the subject, along the body axis of the subject; shielding unit for shielding at least a part of the X-ray beam generated by the X-ray source, thereby acquiring the first projection data; region-setting unit for displaying an image for setting a scan region or an image-generating region, in accordance with the first projection data shielded by the shielding unit; second scan control unit for performing a control, thereby acquiring second projection data while rotating the X-ray source around the subject in accordance with the scan region or the image-generating region set by the region-setting unit; and reconstruction mans for synthesizing the first projection data partly shielded by the shielding unit, with the second projection data, thereby performing a reconstruction process.

Still another object of this invention is to provide a method of controlling an X-ray CT apparatus having an X-ray source which generates an X-ray beam diverging along a body axis of a subject, and X-ray detecting unit including detecting elements arranged in rows, along the body axis of the subject and configured to detect X rays that have passed through the subject. The method comprises: a step of moving the X-ray source, relative to the subject, along the body axis of the subject, and shielding at least a part of the X-ray beam generated by the X-ray source, thereby acquiring first projection data; a step of displaying an image for setting a scan region or an image-generating region, in accordance with the first projection data, and setting the scan region or the image-generating region; a step of rotating the X-ray source around the subject in accordance with the scan region or the image-generating region set, thereby acquiring second projection data; and a step of synthesizing the first projection data with the second projection data, thereby performing a reconstruction process.

Another object of this invention is to provide an X-ray CT apparatus having an X-ray source which generates an X-ray beam diverging along a body axis of a subject, X-ray detecting unit including detecting elements arranged in rows, along the body axis of the subject and configured to detect X rays that have passed through the subject, reconstruction unit for performing back projection on the data about the subject, based on the X-ray beam detected by the X-ray detecting unit, thereby reconstructing an image, and display unit for displaying the image reconstructed by the reconstruction unit. This X-ray CT apparatus comprises: scan control unit for performing control, thereby acquiring first projection data while rotating the X-ray source around the subject, and acquiring second projection data while moving the X-ray source, relative to the subject, along the body axis of the subject, based on a projection direction determined from the first projection data; and reconstruction-process unit for performing a reconstruction process, based on the first projection data and the second projection data.

Another object of the present invention is to provide a method of controlling an X-ray CT apparatus having an X-ray source which generates an X-ray beam diverging along a body axis of a subject, X-ray detecting unit including detecting elements arranged in rows, along the body axis of the subject and configured to detect X rays that have passed through the subject, reconstruction unit for performing back projection on the data about the subject, based on the X-ray beam detected by the X-ray detecting unit, thereby reconstructing an image, and display unit for displaying the image reconstructed by the reconstruction unit. This method comprises: a step of acquiring first projection data, while rotating the X-ray source around the subject; a step of determining, from the first projection data, a projection direction in which to acquire second projection data; a step of acquiring the second projection data, while moving the X-ray source, relative to the subject, along the body axis of the subject, based on a projection direction; and a step of performing a reconstruction process, based on the first projection data and the second projection data.

The present invention can provide an X-ray CT apparatus in which the collimator is operated during a line-orbit scan, reducing the X-ray application to a region that does not contribute to image reconstruction and thus minimizing the X-ray exposure.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a shield diagram showing an X-ray CT apparatus 10 according to a first embodiment of the present invention;

FIG. 15 is a flowchart explaining the sub-routine of determining the angle at which to acquire line-orbit data, performed in Step S13 described in the flowchart of FIG. 14; and FIG. 16 is a flowchart explaining another type of sub-routine of determining the angle at which to acquire line-orbit data, performed in Step S13 described in the flowchart of FIG. 14.

DETAILED DESCRIPTION OF THE INVENTION

Embodiments of the present invention will be described with reference to the accompanying drawings.

First Embodiment

A first embodiment of the present invention will be described.

Figure 2:
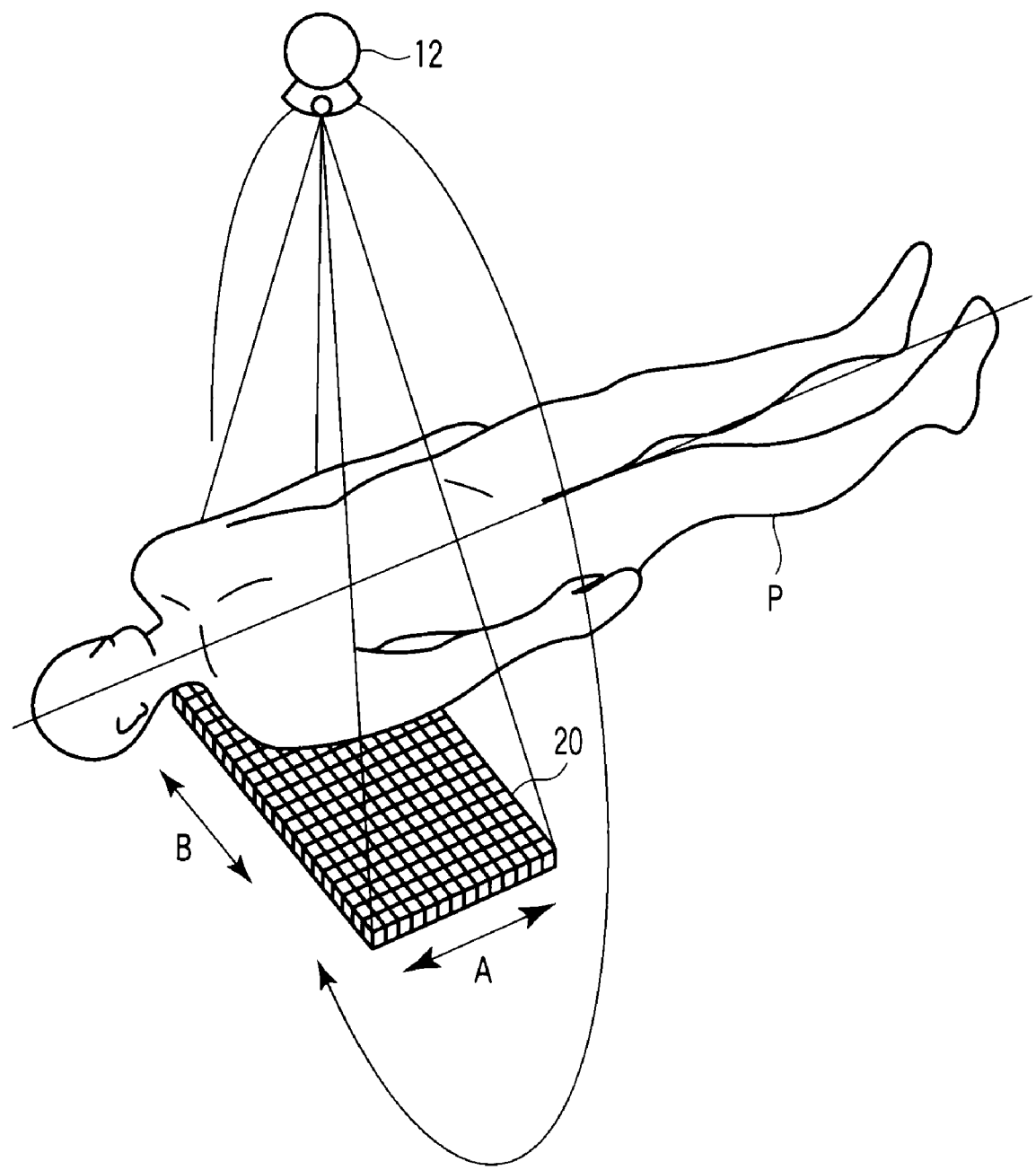
FIG. 2 is a perspective view explaining how the X-ray CT apparatus 10 of FIG. 1 provides tomograms.

FIG. 1 is a shield diagram showing an X-ray CT apparatus 10 according to the first embodiment of this invention. FIG. 2 is a perspective view explaining how the X-ray CT apparatus 10 of FIG. 1 provides tomograms.

Various types of X-ray CT apparatuses are available. One is the rotate/rotate type. Another is the stationary/rotate type. In a further type, the electron beam is deflected, thereby electronically moving the X-ray source on the target. In the rotate/rotate type, the X-ray tube and the detector system rotate together around the subject. In the stationary/rotate type, a number of detecting elements are arranged, forming a ring, and only the X-ray tube rotates around the subject. The technical concept of this invention can be applied to any type of X-ray CT apparatus. In other words, the technical concept of the invention can be applied to any apparatus that has an X-ray tube and a multi-slice scanning detector.

The first embodiment, which will be described below, is a rotate/rotate X-ray CT apparatus, which is the most popular at present. The scan system employed in the first embodiment is a line+cicle reconstruction system in which the line-orbit scan method is performed, as well as the circular-orbit, cone-beam reconstruction method proposed by Feldkamp et al.

As FIG. 1 shows, the X-ray CT apparatus 10 comprises an X-ray tube 12, a rotary ring 14, a collimator plate 16, a bed 18, a two-dimensional detector system 20, a data-acquisition (DAS) circuit 22, a non-contact data transmitter 24, a pre-processing device 26, a gantry drive unit 30, a slip ring 32, a collimator drive mechanism 34, a bed drive unit 36, a high-voltage generator 40, a host controller 42, a storage device 44, an auxiliary storage device 46, a data processor 48, a reconstruction device 50, an input device 54, an image-processing unit 56, a display 58, a network communications device 60, and a data/control bus 62. The data/control bus 62 connects an external image-processing apparatus (not shown) to the X-ray CT apparatus 10.

The X-ray tube 12 is an X-ray source that generates X rays. The X-ray tube 12 is provided on the rotary ring 14. To the X-ray tube 12, the high-voltage generator 40 applies a high voltage via the slip ring 32, so that the subject may be exposed to X rays. Applied with the high voltage, the X-ray tube 12 accelerates electrons, which are bombarded onto the target. Bombarded with the accelerated electrons, the target emits a cone-shaped X-ray beam, which is more precisely shaped like a pyramid, to the subject P lying on the bed 18 that is located in the effective field of view (FOV).

In order to provide high-precision tomograms, it is desired that the X-ray tube 12 be adjusted in position relative to the two-dimensional detector system 20, such that the axis of the X-ray beam aligns with the center of the two-dimensional detector system 20.

Figure 3:
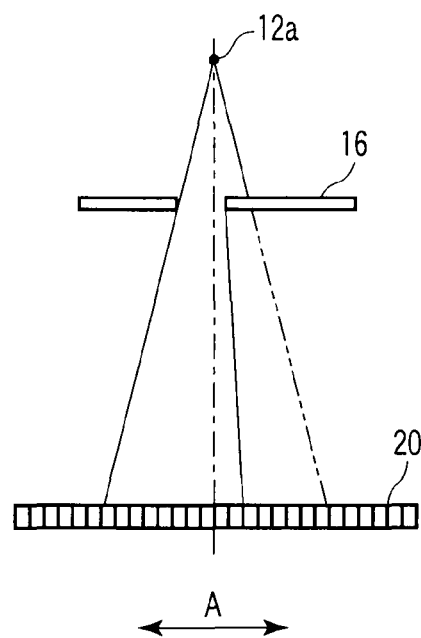
FIG. 3 is a diagram explaining how an X-ray beam is applied from the X-ray tube 11 to the two-dimensional detector system 14 in the apparatus 10 of FIG. 1.

As FIG. 3 shows, the X-ray beam emitted from the X-ray tube 12 is collimated by the collimator plate 16. The collimator plate 16 can be opened and closed as will be described later, when the collimator drive mechanism 34 operates under the control of the host controller 42. In the case illustrated in FIG. 3, the collimator plate 16 shields the right half of the X-ray beam when the collimator plate 16 is moved near the axis of the X-ray beam coming from the focal point 12a of the X-ray tube 12. Thus shielded in part, the X-ray beam can be applied to the subject P in a desired dose.

The rotary ring 14 holds the X-ray tube 12, collimator plate 16, two-dimensional detector system 20 and data-acquisition circuit 22. The rotary ring 14 is driven by the gantry drive unit 30 at a high speed of one revolution or more per second. As the rotary ring 14 is so driven, the X-ray tube 12, collimator plate 16 and two-dimensional detector system 20 rotate at such a high speed around the subject P. The bed 18 is provided to hold the subject P. The X-ray tube 12 and the two-dimensional detector system 20, both provided on the rotary ring 14, are opposed to each other across the bed 18.

The two-dimensional detector system 20 is a detector system designed to detect X rays coming through the subject P. As described above, the system 20 is secured to the rotary ring 14 and opposed to the X-ray tube 12. As shown in FIG. 2, the two-dimensional detector system 20 has a plurality of detecting elements, each composed of a scintillator and a photo-diode. The detecting elements are arranged in rows and columns, forming a two-dimensional matrix. The rows extend in the axial direction A (slice direction) of the subject P, and the columns extend in the channel direction B intersecting at right angles to the axial direction A. Each row consists of, for example, 1000 detecting elements. Hence, the two-dimensional detector system 20 has 1000 channels. (Hereinafter, each row of detecting elements will be referred to as "detecting-element row.") The X-ray CT apparatus 10 has, for example, a 256-row multi structure (thus, is capable of acquiring a 256-row tomogram at a time). (In practice, however, the detecting elements are arranged in 64 rows, 128 rows or 256 rows.) The line+cicle reconstruction system according to this invention is particularly effective if the detector is broad in the slice direction (i.e., the axial direction of the subject, or a direction along the line around which the X-ray tube 12 and two-dimensional detector system 20 rotate) and if the X-ray beam has a large cone angle. The line+cicle reconstruction system is useful if the X-ray CT apparatus 10 has, for example, at least 64 rows of detector elements. The detector elements of the two-dimensional detector system 20 may be arranged, forming either a curved array or a flat array.

The data-acquisition (DAS) circuit 22 has a plurality of DAS chips and receives a great amount of data about the M×N channels, which the two-dimensional detector system 20 has detected. (Hereinafter, M×N channel data for each view will be referred to as "projection data.") The data-acquisition (DAS) circuit 22 amplifies the data signals and performs A/D conversion on the data signals, generating X-ray transmission data. The X-ray transmission data is transmitted to the fixed data-processing unit through the non-contact data transmitter 24 that performs optical communication.

The non-contact data transmitter 24 optically transmits the X-ray transmission data to the next-stage device. The data-acquisition circuit 22 and the non-contact data transmitter 24 are designed to operate as fast as possible to enable the large amount of two-dimensional projection data generated in the two-dimensional detector system 20 to be transmitted without any delay.

That is, the X rays that have passed through the subject P reach the two-dimensional detector system 20. The system 20 converts the X rays to analog electric signals. The data-acquisition circuit 22 converts the electric signals to digital two-dimensional projection data. The projection data is supplied to the pre-processing device 26 that corrects the data in various ways.

The pre-processing device 26 receives the two-dimensional projection data from the non-contact data transmitter 24 and performs pre-processes, such as sensitivity correction and X-ray intensification, on the two-dimensional projection data. The two-dimensional projection data thus processed is supplied directly to the data processor 48 or is temporality stored in the storage device 44 and then supplied to the data processor 48. In the present embodiment, the projection data is stored after it has been pre-processed. Instead, the projection data may be stored before it is pre-processed.

The gantry drive unit 30 performs a drive control, causing the X-ray tube 12 and the two-dimensional detector system 20 to rotate together around an axis parallel to the body axis of the subject who is placed in the diagnosis opening of the X-ray CT apparatus 10. The gantry drive unit 30 may be configured to rotate only the X-ray tube 12 around that axis. The bed drive unit 36 is designed to move the bed 18 on which the subject P is lying, mainly along the body axis of the subject P.

The high-voltage generator 40 applies a high voltage via the slip ring 32, so that the subject may be exposed to X rays. The high-voltage generator 40 comprises a high-voltage transformer, a filament-heating transducer, a rectifier, and a high-voltage switching device. The high voltage generated by the high-voltage generator 40 is applied to the X-ray tube 12 through the slip ring 32.

The host controller 42 performs consolidated control on various processes, such as the photographing process, data-processing, and image-processing. To control the photographing process, for example, the host controller 42 stores the input data representing scan conditions, such as slice thickness, in the internal memory. Based on the scan conditions automatically selected in accordance with the patient ID (or directly set at the manually operated input device 54), the host controller 42 controls the high-voltage generator 40, bed drive unit 36, gantry drive unit 30 and X-ray tube 12. The host controller 42 also controls the distance and speed for and at which the bed 18 is moved along the body axis, the opening and closing of the collimator plate 16, the rotation speed and rotation pitch of the two-dimensional detector system 20, and the timing of applying X rays to the subject P. A cone-shaped X-ray beam that diverges in the slice direction is thereby applied to the region of interest of the subject P. As a result, the detecting-element rows are irradiated with X rays coming in various directions, whereby projection data is acquired. Further, the host controller 42 performs a reconstruction process on the projection data thus acquired, generating an X-ray CT image.

The host controller 42 also controls the switching of the switches provided in the two-dimensional detector system 20, in accordance with the scan conditions. More precisely, the host controller 42 switches the connection between the detecting elements and the data-acquiring elements, all provided in the detector system 20, thereby combining the X-ray transmission data items detected by the respective detecting elements, in prescribed units. Then, the host controller 42 supplies the resulting X-ray transmission data to the next-stage component, i.e., the data-acquisition circuit 22. The data-acquisition circuit 22 performs a prescribed process on the X-ray transmission data.

The auxiliary storage device 46 is a device having a storage area that is large enough to hold the reconstructed image data the reconstruction device 50 has generated.

The data processor 48 has a computer circuit incorporating, for example, a CPU. The data processor 48 holds the projection data acquired by the two-dimensional detector system 20. The data processor 48 adds all projection data items acquired in various directions as the photographing system (i.e., X-ray tube 12, collimator plate 16 and two-dimensional detector system 20) rotates, providing multi-direction data. If necessary, the data processor 48 performs interpolation and correction on the multi-direction data.

The reconstruction device 50 performs a reconstruction process on the projection data generated by the data processor 48, thereby generating reconstructed image data representing a predetermined slice. To be more specific, the reconstruction device 50 reconstructs a two-dimensional image, based on the assumption that the X rays are parallel and neglecting the cone angle to the slice direction, or a three-dimensional image, in consideration of the cone angle of the X-ray path to the slice direction as in the Feldkamp et al. method. Moreover, the reconstruction device 50 reconstructs data presenting the two-dimensional distribution of X-ray absorption coefficients for the sections of the subject, which extend across the body axis, or data representing the three-dimensional distribution of X-ray absorption coefficients (i.e., group of boxels, known as "boxel-volume data," each boxel being three-dimensional volume data). Note that the reconstruction device 50 performs so-called real time reconstruction, reconstructing a tomogram from multi-direction projection data in a shorter time than the time required to acquire this multi-direction projection data.

The input device 54 has a keyboard, various switches, and a mouse. When operated by an operator, it can input various scan conditions such as the slice thickness and the number of slices required.

The image-processing unit 56 performs image-processing for displaying a tomogram, including window conversion and RGB process, generating display-image data. The display-image data is supplied to the display 58. The image-processing unit 56 also generates so-called pseudo-three-dimensional image data representing a tomogram of a given section, a protection image with respect to a given direction and a three-dimensional surface image. The pseudo-three-dimensional image data is output to the display 58. The display 58 displays an X-ray CT image represented by the pseudo-three-dimensional image data.

The network communications device 60 exchanges information with an apparatus provided outside the X-ray CT apparatus 10, via a network such as a private LAN or the Internet. Particularly, the network communications device 60 transmits the image data generated in the network communications device 60 and receives the maintenance information for the apparatus 10, through the Internet or the like.

The arithmetic operations related to the image reconstruction, section conversion, image displaying and the like are performed in the X-ray CT apparatus 10 as in the most cases. These operations may be performed in any external image-processing apparatus such as a workstation. In this case, the data transmitted to the external image-processing apparatus from the X-ray CT apparatus 10 can be one that represents a reconstructed image, one that does not represent a reconstructed image, or one that can be displayed as a tomogram. Whichever type is transmitted from the X-ray CT apparatus 10, the present embodiment can achieve its advantages.

In most X-ray CT apparatuses, a scannogram (i.e., an X-ray transmission image used to set a photographing position) is acquired in preparation for scanning. In the line+circle reconstruction method, a line-orbit scan is therefore carried out after acquiring the scannogram, thereby acquiring the projection data (hereinafter referred to as "line-orbit data") that pertains to the line orbit. Then, a circular-orbit scan is performed, acquiring projection data (hereinafter referred to as "circular-orbit data") that pertains to the circular orbit. From the line-orbit data and the circular-orbit data, a reconstructed image that is free of artifacts will be formed.

Instead of the line-orbit data, helical-orbit data acquired by performing a helical-orbit scan may be synthesized with the circular-orbit data, thereby to accomplish the image-reconstructing process. Further, the line-orbit data may not be used, and the gantry may be stopped in the helical orbit to reconstruct the image.

Figure 4A:
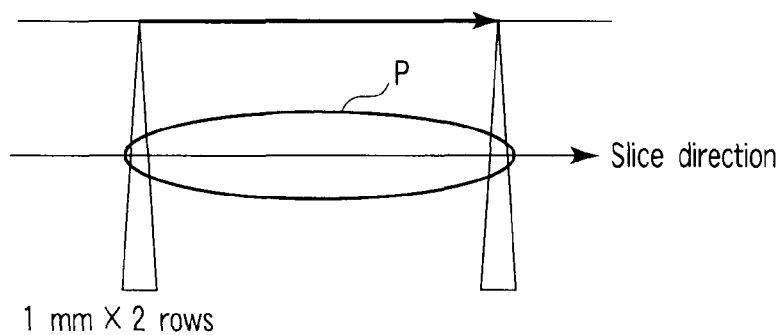
FIG. 4A is a diagram explaining a method of acquiring data in the form of a scannogram in the X-ray CT apparatus according to the first embodiment of this invention.
Figure 4B:
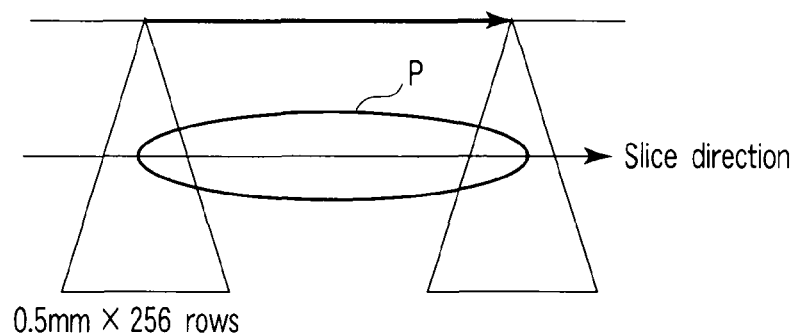
FIG. 4B is a diagram explaining a method of acquiring line-orbit data in the X-ray CT apparatus.

The data acquisition using a scannogram is performed at a small cone angle of, for example, 1 mm×2 rows as is illustrated in FIG. 4A. On the other hand, the method of acquiring line-orbit data requires a large cone angle of, for example, 0.5 mm×256 rows as illustrated in FIG. 4B. The acquisition of a scannogram and the acquisition of line data are equivalent in that the data is acquired while the gantry remains stopped. Thus, the line data may be acquired instead of a scannogram, and a scannogram can be formed from that part of the line data which pertains to the center rows.

A region in which to acquire line data and the operation of the collimator plate 16 will be explained, with reference to FIGS. 5 to 7.

Figure 5:
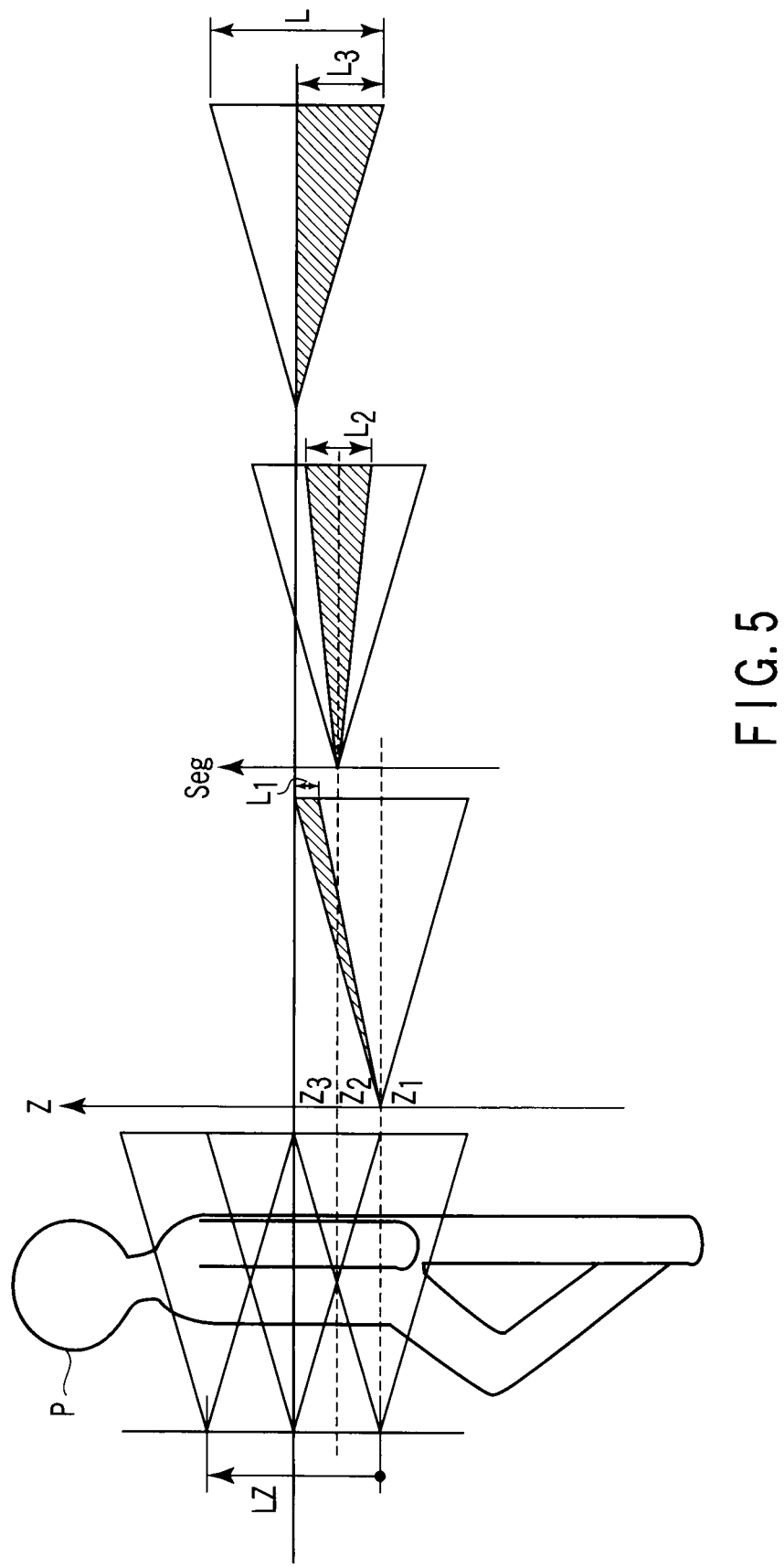
FIG. 5 is a diagram explaining a region in which to acquire line data and the operation of the collimator plate 16, and showing the relation between that region and the parts of the data, which contribute to image reconstruction.

In FIG. 5, LZ indicates a region in which to acquire line data from the subject P, and L indicates that part of the line data which has a preset cone angle. Only a part of the line data contributes to the reconstruction. In other words, only a part of the line data is used to reconstruct an image. For example, at $Z_1$, the shaded part $L_1$ of the line data L is used; at $Z_2$, the shaded part $L_2$ of the line data L is used; and at $Z_3$, the shaded part $L_3$ of the line data L is used. That is, parts other than parts $L_1$, $L_2$ and $L_3$ do not contribute to the reconstruction. Therefore, the collimator plate 16 may shield the parts of the X-ray beam corresponding to those parts of the line data which are not used to reconstruct an image.

In this case, the part of the data to be used changes as the X-ray tube 12 moves in the Z-axis direction (scan direction). Thus, in accordance with this change, the host controller 42 controls the collimator drive mechanism 34. So driven, the mechanism 34 slides the collimator plate 16, adjusting the opening through which the X-ray beam travels toward the two-dimensional detector system 20.

Figure 6:
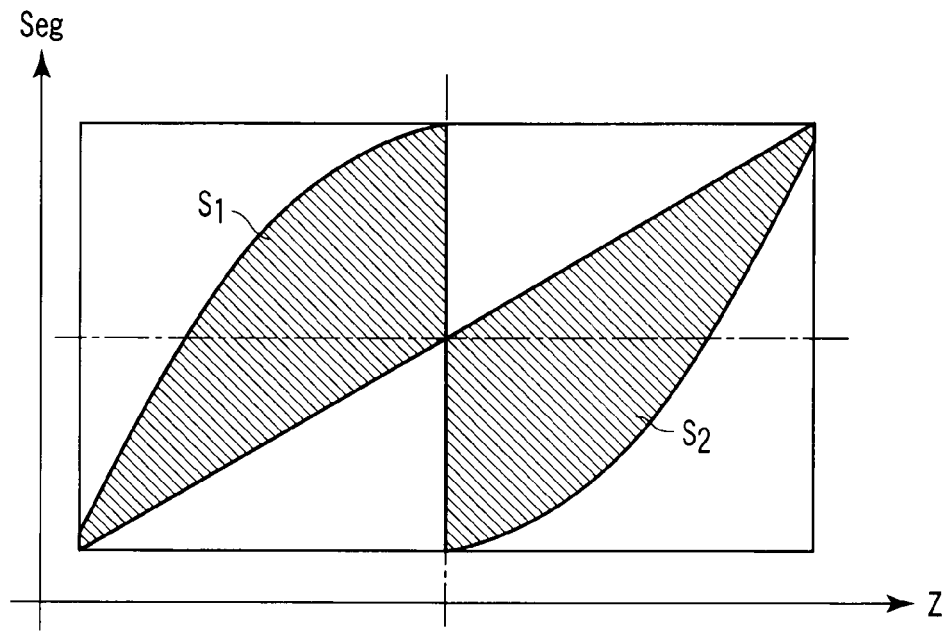
FIG. 6 is a diagram showing that part of the line data actually used for a scan surface.

FIG. 6 is a diagram showing those parts of the line data which are used for a scan surface. In FIG. 6, the shaded regions $S_1$ and $S_2$ indicate those parts of the data which are used. Any parts other than parts of the data, i.e., the regions other than shaded regions $S_1$ and $S_2$, do not contribute to the image reconstruction, though they are acquired as line data. Hence, it suffices to adjust the opening defined by the collimator plate 16 in accordance with the shaded regions $S_1$ and $S_2$, i.e., data parts that are to reconstruct the image. As can be seen from FIG. 6, at whichever Z position, only half of the data or a smaller part thereof contributes to the reconstruction.

The shaded regions $S_1$ and $S_2$, i.e., data parts that should be acquired at all, can change in accordance with the data-acquiring position (in the direction of the body axis). The parts of data which are actually used are determined by the scanning conditions, the size and position of the ROI image reconstructed, the tilt angle of the gantry, the line-data acquiring direction, and the like. Nonetheless, the shaded regions $S_1$ and $S_2$ shown in FIG. 6 are representative examples of the data parts.

Figure 7:
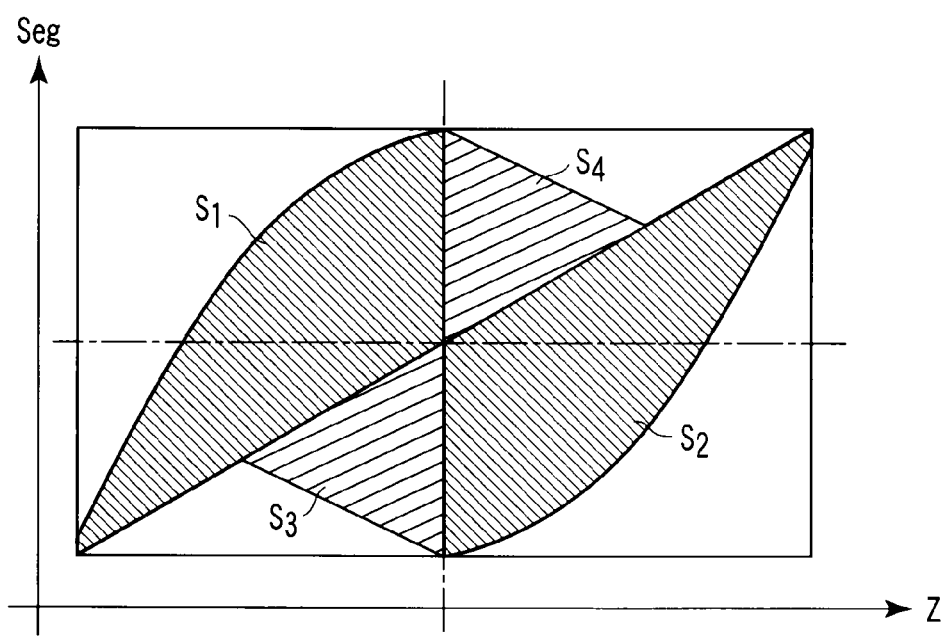
FIG. 7 is a diagram illustrating shaded regions $S_1$, $S_2$, $S_3$ and $S_4$ that corresponds to the parts of data not shielded by the collimator plate 16 and actually contributing image reconstruction.

FIG. 7 is a diagram showing those parts of the X-ray beam which the collimator plate 16 actually shields, so that shaded regions $S_1$ and $S_2$, both shown in FIG. 6 and some other regions may contribute to the image reconstruction.

To acquire data that is necessary in the light of the principle of image reconstruction, the collimator plate 16 should shield parts of the X-ray beam other than those that correspond to the shaded regions $S_1$ and $S_2$. In practice, however, it is difficult to shield only the parts of the X-ray beam which do not contribute to the image reconstruction. In view of the response of the collimator plate 16 to an opening-closing signal, a practical method is to shield all parts of the beam but the shaded regions $S_1$ and $S_2$ and two following regions $S_3$ and $S_4$, as shown in FIG. 7. The "following regions $S_3$ and $S_4$" are regions exposed to X rays, though do not correspond to data parts used, in order to avoid a highly controlled motion of the collimator plate 16.

In the case shown in FIG. 7, the collimator plate 16 is moved linearly. The manner of moving the collimator plate 16 is not limited to this. For example, the control points may be increased in number and the collimator plate 16 may be non-linearly moved. If this is the case, those parts of the X-ray beam which correspond to the data parts not used can be more precisely shielded.

Figure 8:
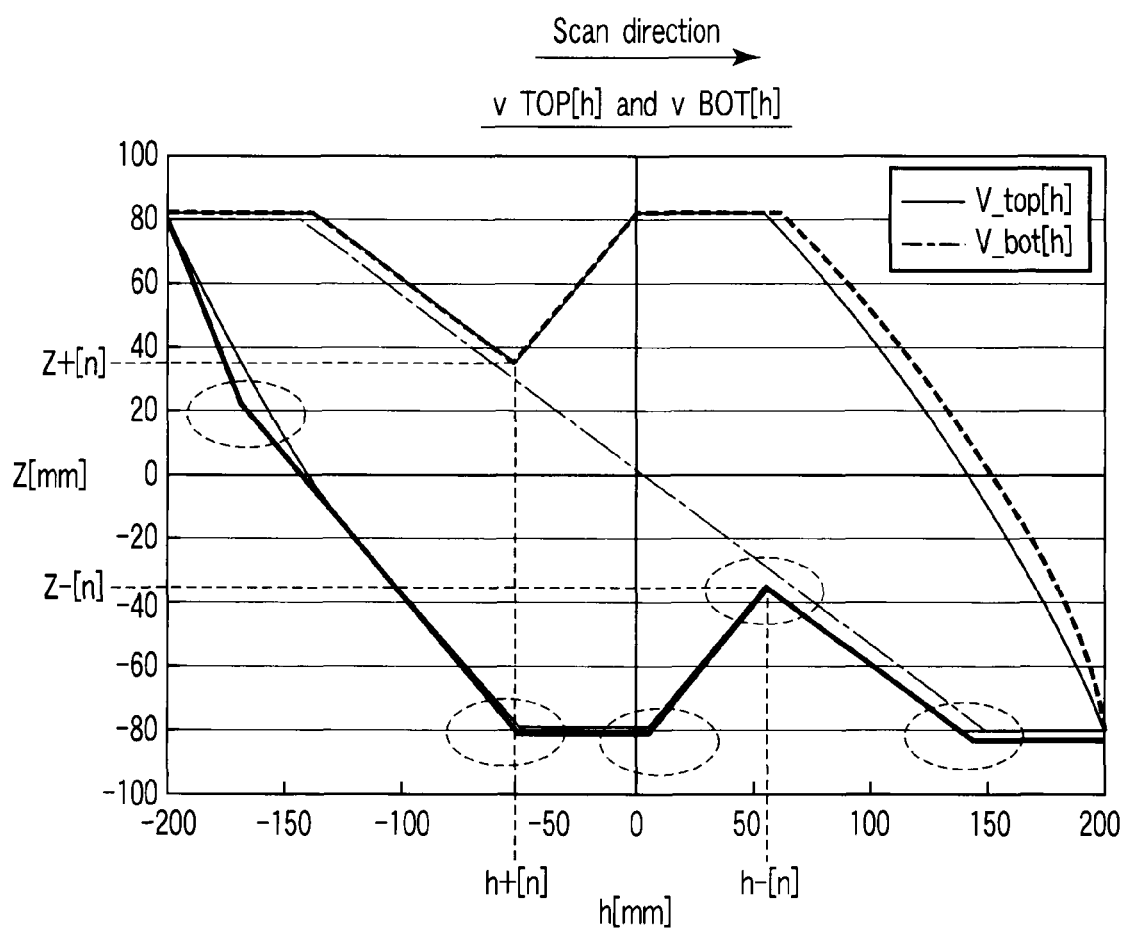
FIG. 8 is a diagram showing those parts of the data, which are actually used for a scan surface, the other parts of the data having been shielded by the collimator plate 16 minutely controlled.

FIG. 8 is a diagram showing those parts of the data which are actually used for a scan surface, the other parts of the data having been shielded by the plate 16 minutely controlled. In FIG. 8, plotted on the ordinate axis is the distance (mm) the collimator plate 16 is moved along the body axis (in the slice direction), forward and backward from the reference position (distance 0), and plotted on the abscissa axis is the distance (mm) the plate 16 is moved along the channel direction (scan direction).

The operating lines shown in FIG. 8 change, each in accordance with the number of the detecting elements that constitute the two-dimensional detector system 20 (e.g., 256, 128, 64, . . . )

Figure 9:
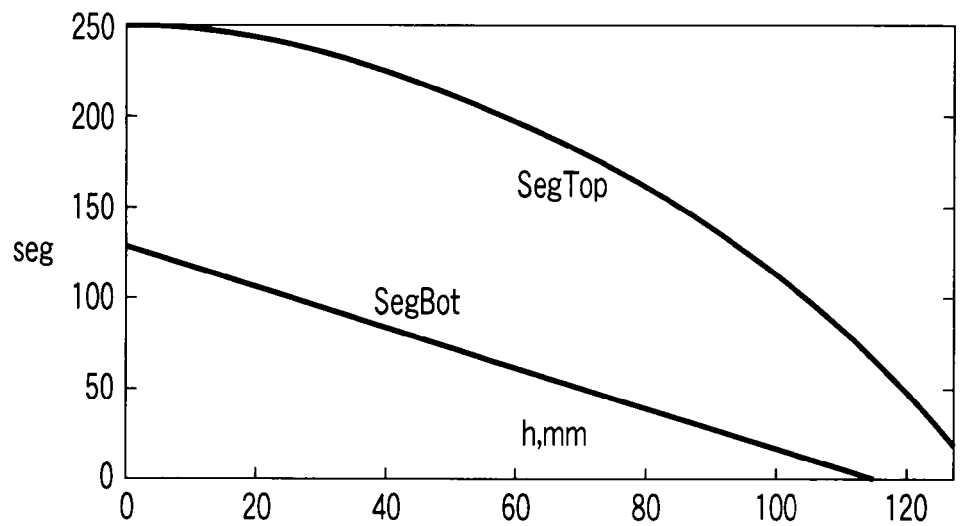
FIG. 9 is a magnified view of a part of the opening/closing characteristic of the collimator plate 16, which is illustrated in FIG. 8.

FIG. 9 is a magnified view of a part of the opening/closing characteristic of the collimator plate 16 which is illustrated in FIG. 8. In FIG. 9, plotted on the ordinate axis is the number of the segments constituting the projection data, and plotted on the abscissa axis is the distance h (mm) at which the plate 16 lies in the slide direction from the center of the scan surface. In FIG. 9, SegTop and SegBot are, respectively, the upper and lower limits to the number of the segments constituting the projection data.

Figure 10:
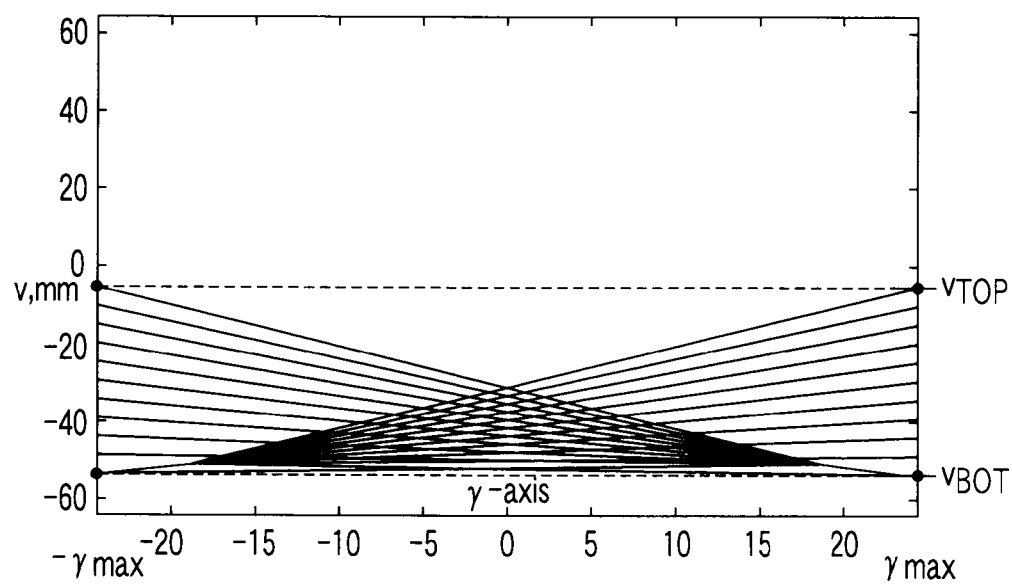
FIG. 10 is a characteristic diagram explaining an example of a collimation width set.

Assume that the collimator plate 16 is at distance h of 100. Then, the collimation width is set as illustrated in FIG. 10. In FIG. 10, part $v_{TOP}$ to $v_{BOT}$, is a part that is used as data. The positions of parts $v_{TOP}$ and $v_{BOT}$ are determined from SegTop and SegBot (FIG. 9), respectively.

FIG. 10 is a characteristic diagram explaining an example of a collimation width set. In FIG. 10, plotted on the ordinate axis is the distance (mm) the detector assumes in the slice direction, and plotted on the abscissa axis is the fan angle (°) defined between the center channel and the channel in question. The region above part $v_{TOP}$ is that part of the X-ray beam which is shielded by the collimator plate 16. The lines drawn between $v_{TOP}$ and $v_{BOT}$ indicate filtering directions. The projection data items on these lines are indispensable to the image reconstruction. While the collimator plate 16 is being moved to acquire these projection data items and to shield those parts of the X-ray beam which correspond to the unnecessary data parts, the scanning is performed.

Figure 11:
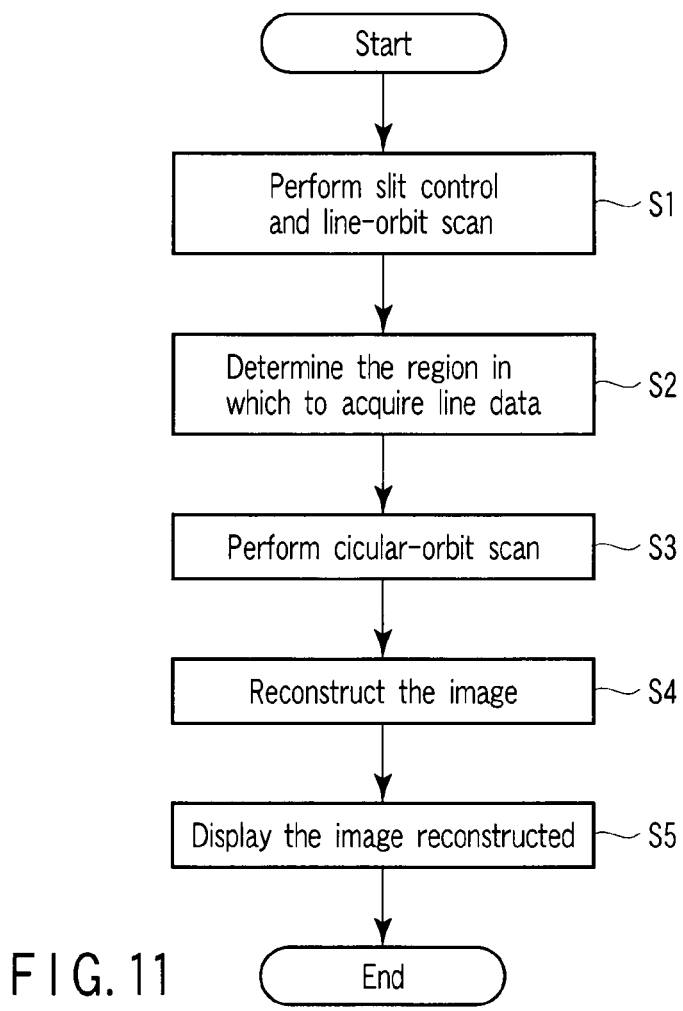
FIG. 11 is a flowchart explaining the basic operation of the X-ray CT apparatus according to the first embodiment of this invention.

FIG. 11 is a flowchart explaining the basic operation of the X-ray CT apparatus according to the first embodiment of this invention.

The basic operation of the X-ray CT apparatus according to this embodiment will be explained with reference to the flowchart of FIG. 11.

First, in Step S1, the X-ray tube 12 applies X rays to the subject, whereby a line-orbit scan is performed. Line-orbit data is thereby acquired. At the same time, the collimator drive mechanism 34 is driven, controlling the motion of the collimator plate 16. Thus controlled, the collimator plate 16 shields those parts of the X-ray beam which do not contribute to the image reconstruction.

The number of line-orbit data rows, the acquisition thickness, the voltage applied to the X-ray tube and the tilt angle of the gantry must be identical to those used in the circular-orbit scan. They are therefore determined uniquely. If the conditions of performing the line-orbit scan are different from the conditions of the circular-orbit scan, which have been already set, the line+circle reconstruction cannot be accomplished.

An alarm is therefore generated, informing the operator of this fact. The alarm may be a message displayed on the display 58 or an aural message (not displayed). Whether or not the conditions for the reconstruction are appropriate may be determined from the ID data of the patient, the data about the part to photograph, the date of photographing, and the like, as well as the above-mentioned scan conditions.

The line-orbit data thus acquired in Step S1 is stored in the storage device 44. At this point, the scan conditions are also stored in association with the line-orbit data.

Next, in Step S2, a region in which to acquire line data from the subject P is determined. A scannogram (i.e., image which is used in determining this region) is generated from line-orbit data items. The line-orbit data items are two-dimensional projection data items acquired from a plurality of positions, i.e., various photographing positions. They have been acquired, each overlapping another in the slice direction.

The scannogram has been generated by extracting projection data items having a small cone angle to the slice direction from the respective two-dimensional projection data items acquired at various positions and then synthesizing the projection data items thus extracted. In other words, a scannogram is generated, first by extracting projection data items acquired at the detecting-element rows which are at the middle with respect to the slice direction, from the two-dimensional projection data acquired at each photographing position, and then by arranging these projection data items in the slice direction, each at a specific position. A marker is displayed on the scannogram. The marker can be moved to set the region in which to generate an image or in which to perform a scan.

The line-orbit data may not be sufficient to reconstruct an image for the region or the scan region, either having been set as described above. In this case, an alarm is generated or the operation is inhibited from proceeding further. Whether the line-orbit data is sufficient is determined in accordance with whether line-orbit data is available for the region that can be found by a method described later.

The region in which to acquire line-orbit data is determined uniquely by the size and position of the ROI the image of which should be reconstructed. That is, the region is the function of the calibration FOV, tilt angle, presence or absence of a mask in the interpolated part, reconstruction region, scan position and line-data acquiring direction (position of the X-ray tube). The calculation for determining this region is performed by the host controller 42, the data processor 48, and the like, though is not explained here in detail.

Once the region in which to acquire line-orbit data has been thus determined, a circular-orbit scan is performed in Step S3 in the region, acquiring circular-orbit data. The circular-orbit data is stored in the storage device 44. At this point, the scan conditions used are stored in association with the circular-orbit data. Using the data acquired in the line-orbit scan performed in Step S1 and the data acquired in Step S3, the reconstruction device 50 reconstructs an image in Step S4. The method the device 50 employs to reconstruct an image is known, and will not be explained in detail.

In Step S5, the display 58 displays the image the device 50 has reconstructed.

The X-ray CT apparatus 10 can operate in a modified way, which differs from the sequence of steps shown in the flowchart of FIG. 11.

Assume that when the operation sequence is started, a scan plan is set, determining the scan order and the scan conditions. Then, the line-orbit scan conditions and the circular-orbit scan conditions are set for the image reconstruction. The line-orbit scan conditions are compared with the circular-orbit scan conditions. If the line-orbit scan conditions do not match with the circular-orbit scan conditions, the apparatus 10 generates an alarm, indicating this fact. Alternatively, the apparatus 10 is prevented from preceding to the next step.

The operation sequence can be switched or changed at the operator's discretion.

The above-mentioned conditions for acquiring line data, such as the data-acquisition thickness, the number of rows, the voltage applied to the X-ray source, and further the tilt angle of the gantry, and also the acquisition-start position and the acquisition length must be the same for both the line-orbit scan and the circular-orbit scan. It does not matter, nonetheless, whether these conditions are set by the operator or the high-voltage generator 40 and the like.

Thus, the addition X-ray exposure can be minimized since the collimator plate 16 shields parts of the X-ray beam other than the parts which contribute to the image reconstruction.

Second Embodiment

A second embodiment of the present invention will be described.

The second embodiment, which will be described below, is identical to the first embodiment described above, in terms of the basic configuration and operation of the X-ray CT apparatus. To avoid repeated explanations, the components identical to those of the first embodiment are designated by the same reference numbers and will not be shown or described. Only the components that characterize the second embodiment will be described.

Figure 12:
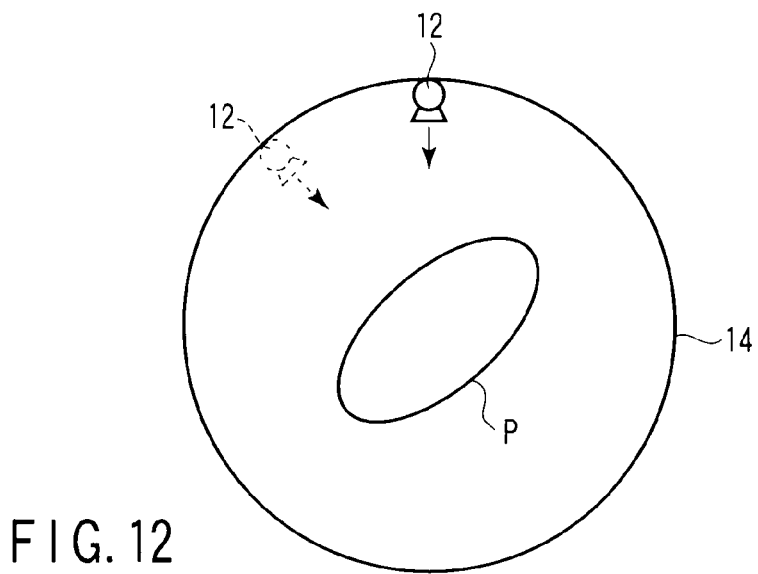
FIG. 12 is a diagram explaining the direction in which the line data is acquired in an X-ray CT apparatus according to a second embodiment of the present invention.

As indicated above, the X-ray tube 12 is provided on the rotary ring 14. Therefore, the direction in which to acquire line data (i.e., position of the X-ray tube) can be freely set. X rays can therefore be applied to the subject P in any direction (from any position) as shown in FIG. 12. That is, the distance the X rays travel through the subject P varies as the X-ray tube 12 is moved. The shorter this distance, the smaller will be the amount of the line data. In other words, if the X rays are applied in such a direction to travel the shortest possible distance through the subject P, the X-ray dose applied to the subject P can be minimized.

To acquire data from one of the subject's shoulders or abdomen, the distance the X rays travel through the subject P in the photographing direction (i.e., AP direction) is longer than the distance the X rays travel in the direction (i.e., LR direction) perpendicular to the photographing direction. This can also be confirmed by the projection data acquired by performing a circular-orbit scan.

The photons defining certain projection data are counted. The photon count may be the smallest if the X-ray tube 12 applies an X-ray beam at a particular angle to the body surface of the subject P. It is desirable to apply the X-ray beam at such an angle, because the X-ray dose will be minimal and the line data acquired will be least influenced by noise.

Figures 13, 14:
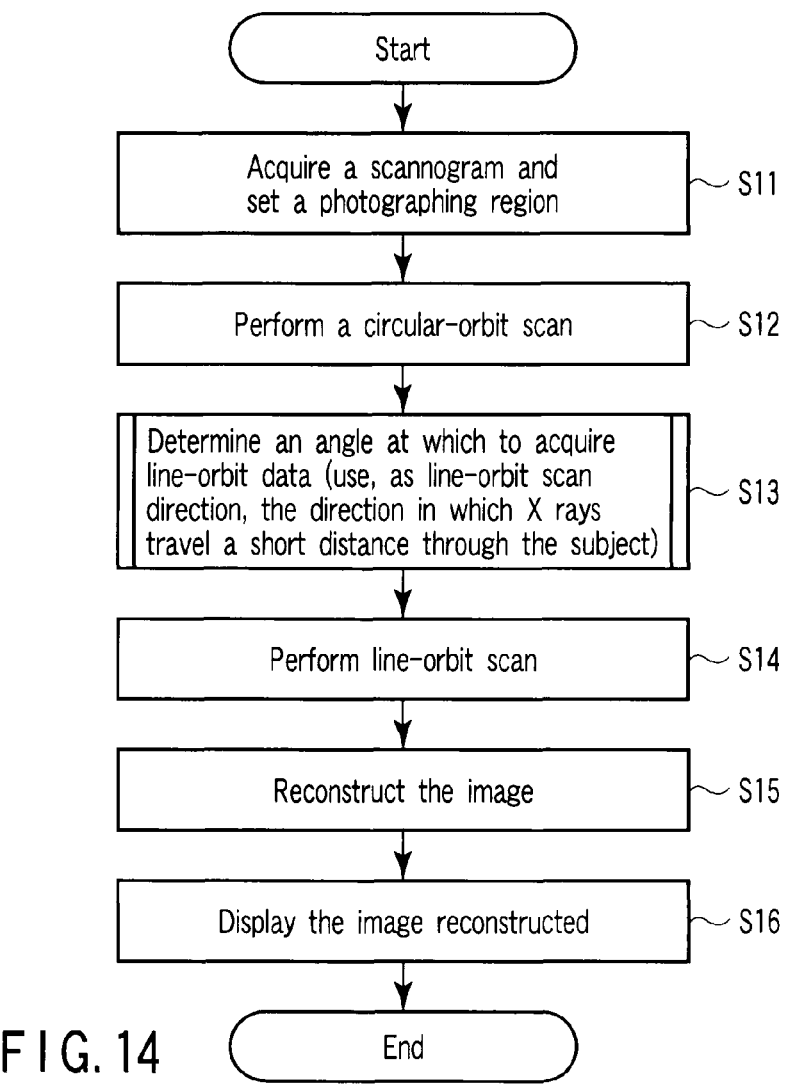
FIG. 13 is a diagram explaining how to determine an angle at which to acquire line-orbit data.
FIG. 14 is a flowchart explaining the basic operation of the X-ray CT apparatus according to the second embodiment of this invention.

Consider two directions in which the X rays may be applied to the subject P, as shown in FIG. 13. In view of the efficiency of acquiring line data, it is better to apply the X rays from above. This is because the maximum data attenuation is small if the X rays are applied in this direction.

To determine the position of the X-ray tube, the photograph data of the circular orbit may be utilized. That is, the line-orbit data is acquired after the circular-orbit data has been acquired. If the cumulative value of the projection data items of the circular orbit is used, the direction in which the X rays should be applied to travel the shortest direction through the subject P can be determined.

The basic operation of the X-ray CT apparatus according to the second embodiment of this invention will be explained with reference to the flowchart of FIG. 14.

First, in Step S11, X rays are applied, acquiring a scannogram and setting the region, in preparation for a line-orbit scan. The region is uniquely determined by the size and position of the ROI the image of which should be reconstructed. That is, the region is the function of the calibration FOV, tilt angle, presence or absence of a mask in the interpolated part, reconstruction region, scan position and line-data acquiring direction (position of the X-ray tube). The calculation for determining this region is performed by the host controller 42, the data processor 48, and the like, though is not explained here in detail.

Next, in Step S12, X rays are applied from the X-ray tube 12 to the photographing region set in Step S11, acquiring circular-orbit data. The circular-orbit data acquired in Step S12 is stored in the storage device 44. At this point, the scan conditions used are stored in association with the circular-orbit data.

Using the data acquired in the line-orbit scan performed in Step S1 and the data acquired in Step S3, the reconstruction device 50 reconstructs an image. The method the device 50 employs to reconstruct an image is known, and will not be explained in detail.

In Step S13, an angle at which to acquire line-orbit data is determined from the data acquired in the circular-orbit scan performed in Step S12. That is, the position of the X-ray tube 12 is determined such that the X rays it emits travel a short distance through the subject P during the line-orbit scan.

FIG. 15 is a flowchart explaining, in detail, the sub-routine of determining the angle at which to acquire line-orbit data, performed in Step S13 described in the flowchart of FIG. 14.

First, in Step S21, the maximum value of certain projection data is calculated from the results of the circular-orbit scan performed in Step S12 shown in FIG. 14. Next, in Step S22, the position where the value calculated in Step S21 becomes minimal. From this position, line data is acquired. Thereafter, the operation goes to Step S24 shown in the flowchart of FIG. 14.

In Step S14, a line-orbit scan is performed based on the data-acquiring angle determined in Step S13. In Step S15, the reconstruction device 50 reconstructs an image. The method the device 50 employs to reconstruct an image is known, and will not be explained in detail.

In Step S16, the display 58 displays the image the device 50 has reconstructed.

In the second embodiment, the line data is acquired by using the maximum value of the projection data, in order to determine the angle at which to acquire the line-orbit data. Instead, volume data may be used to acquire line data in such a sub-routine as illustrated in FIG. 16.

FIG. 16 is a flowchart explaining, in detail, another type of sub-routine of determining the angle at which to acquire line-orbit data, performed in Step S13 described in the flowchart of FIG. 14.

In this sub-routine, the line data is acquired in Step S31, from the results of the circular-orbit scan performed in Step S12 shown in the flowchart of FIG. 14. Thereafter, the operation goes to Step S14 shown in the flowchart of FIG. 14.

In the present embodiment, the line data is thus acquired from in the direction the X rays travels the shortest distance through the subject P. Therefore, the exposure dose pertaining to the line data can be minimized, suppressing the additional exposure.

Not only the line data is acquired from the circular-orbit data described above, but also the direction of acquiring the line data may be determined in accordance with the region of interest. In photographing, for example, one of the subject's shoulders, the distance the X rays travel the shortest distance through the shoulder subject P if applied in the direction of 12 o'clock or 6 o'clock, as is known in the art. Therefore, the gantry drive unit 30 may be so controlled that the X-ray tube 12 applies X rays in the direction of 12 o'clock or 6 o'clock.

The X-ray CT apparatuses according to the first and second embodiments can, of course, be combined in the present invention.

Embodiments of the present invention have been described. The present invention is not limited to the embodiments, nevertheless. Various changes and modifications can, of course, be made without departing from the scope and spirit of the invention.

Further, the embodiments described above include various phases of the invention. The components disclosed herein may be combined in various ways to make various inventions. Even if some of the components of those described above are not used, it may be possible to achieve the object specified above. Any configuration not using some of the components can be considered as an invention so long as it achieves at least one of the advantages that are stated in the "Advantages of the Invention."

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
    an X-ray source which generates an X-ray beam diverging along a body axis of a subject;
    an X-ray detecting unit including detecting elements arranged in rows along the body axis of the subject and configured to detect X rays that have passed through the subject;
    a scan control unit for performing control, thereby acquiring first projection data while moving the X-ray source, relative to the subject, along the body axis of the subject, and acquiring second projection data while rotating the X-ray source around the subject, and determining parts of the first projection data that contribute to image reconstruction;
    an X-ray shielding unit for changing, while the first projection data is being acquired, an amount by which the X-ray beam generated by the X-ray source is shielded in accordance with a position where the first projection data is acquired and the determined parts of the first projection data that contribute to image reconstruction; and
    a reconstruction unit for synthesizing the first projection data partly shielded by the X-ray shielding unit, with the second projection data, thereby performing a reconstruction process.

2. The X-ray CT apparatus according to claim 1, wherein the first projection data pertains to a non-circular orbit, and the second projection data pertains to a circular orbit; the reconstruction unit uses the first projection data and the second projection data, thereby performing reconstruction that reduces cone-beam artifacts; the X-ray shielding unit has an X-ray shielding member; and the X-ray shielding member is moved in accordance with the position where the first projection data is acquired, thereby to acquire the first projection data that is necessary in the reconstruction.

3. The X-ray CT apparatus according to claim 1, further comprising a shielding control unit for changing the amount by which the X-ray beam is shielded by the X-ray shielding unit; and the shielding control unit controls opening and closing of the X-ray shielding unit.

4. The X-ray CT apparatus according to claim 3, wherein the X-ray shielding unit has at least first and second X-ray shielding units which are spaced in a scan direction; the shielding control unit opens the first X-ray shielding unit from a scan-starting position of the X-ray source to a halfway position between the scan-starting position and a scan-ending position of the X-ray source, closes the second X-ray shielding unit from the scan-starting position to a first prescribed position, and opens the second X-ray shielding unit from the first prescribed position to the halfway position; and the shielding control unit opens the first X-ray shielding unit from the halfway position to a second prescribed position, closes the first X-ray shielding unit from the second prescribed position to the scan-ending position, and opens the second X-ray shielding unit from the halfway position to the scan-ending position.

5. An X-ray CT apparatus comprising:
   an X-ray source which generates an X-ray beam diverging along a body axis of a subject;
   an X-ray detecting unit including detecting elements arranged in rows along the body axis of the subject and configured to detect X rays that have passed through the subject;
   a reconstruction unit for performing back projection on the data about the subject, based on the X-ray beam detected by the X-ray detecting unit, thereby reconstructing an image, and a display unit for displaying the image reconstructed by the reconstruction unit;
   a scan control unit for performing control, thereby acquiring first projection data while rotating the X-ray source around the subject, and acquiring second projection data while moving the X-ray source, relative to the subject, along the body axis of the subject, based on a projection direction determined from the first projection data; and
   a reconstruction-process unit for performing a reconstruction process, based on the first projection data and the second projection data,
   wherein the scan control unit acquires the second projection data in a photographing direction based on and after acquiring the first projection data, the first projection data utilized to determine the photographing direction in which the X-ray beam travels a shortest distance through the subject.

6. The X-ray CT apparatus according to claim 5, wherein the scan control unit finds a maximum value from the first projection data, thereby determining the photographing direction.

7. The X-ray CT apparatus according to claim 5, wherein the scan control unit reconstructs volume data from the first projection data and determines the photographing direction from the volume data.

8. A method of controlling an X-ray CT apparatus including an X-ray source which generates an X-ray beam diverging along a body axis of a subject, an X-ray detecting unit including detecting elements arranged in rows along the body axis of the subject and configured to detect X rays that have passed through the subject, a reconstruction unit for performing back projection on the data about the subject, based on the X-ray beam detected by the X-ray detecting unit, thereby reconstructing an image, and a display unit for displaying the image reconstructed by the reconstruction unit, the method comprising:
   acquiring first projection data, while rotating the X-ray source around the subject;
   determining, from the first projection data, a projection direction in which to acquire second projection data;
   acquiring the second projection data, while moving the X-ray source, relative to the subject, along the body axis of the subject, based on a projection direction; and
   performing a reconstruction process, based on the first projection data and the second projection data,
   wherein the acquiring the second projection data is based on and after acquiring the first projection data, and the first projection data is utilized to determine a photographing direction in which the X-ray beam travels a shortest distance through the subject.

* * * * *